(12) United States Patent
Patel et al.

(10) Patent No.: US 7,776,355 B2
(45) Date of Patent: Aug. 17, 2010

(54) DELIVERY SYSTEM FOR TOPICAL MEDICATIONS

(75) Inventors: Bhiku G. Patel, Chandler, AZ (US); Mohan Vishnupad, Easton, CT (US); Eugene H. Gans, Westport, CT (US); Kuljit S. Bhatia, Chandler, AZ (US)

(73) Assignee: Medics Pharmaceutical Corporation, Scottsdale, AZ (US)

( * ) Notice: Subject to any disclaimer, the term of this patent is extended or adjusted under 35 U.S.C. 154(b) by 1074 days.

(21) Appl. No.: 10/613,698

(22) Filed: Jul. 3, 2003

(65) Prior Publication Data

US 2005/0100585 A1 May 12, 2005

(51) Int. Cl.
*A61F 13/00* (2006.01)
*A61K 8/00* (2006.01)

(52) U.S. Cl. .................. 424/443; 424/449; 424/401
(58) Field of Classification Search .................. 424/402, 424/442, 400, 443, 449, 401
See application file for complete search history.

(56) References Cited

U.S. PATENT DOCUMENTS

| | | | |
|---|---|---|---|
| 3,852,210 A | 12/1974 | Krezanoski | |
| 4,545,990 A | 10/1985 | Le Foyer de Costil et al. | |
| 4,803,228 A | 2/1989 | Jacquet et al. | |
| 4,891,228 A | 1/1990 | Thaman et al. | |
| 4,906,617 A | 3/1990 | Jacquet et al. | |
| 4,917,891 A | 4/1990 | Kaufmann et al. | |
| 4,960,772 A | 10/1990 | Sebag et al. | |
| 4,978,695 A | 12/1990 | Hoshino et al. | |
| 5,019,567 A | 5/1991 | Philippe et al. | |
| 5,254,109 A | 10/1993 | Smith et al. | |
| 5,368,581 A | 11/1994 | Smith et al. | |
| 5,387,363 A | 2/1995 | Distaso | |
| 5,409,706 A | 4/1995 | Ramirez et al. | |
| 5,417,674 A | 5/1995 | Smith et al. | |
| 5,445,823 A | 8/1995 | Hall et al. | |
| 5,466,456 A | 11/1995 | Glover | |
| 5,470,884 A | 11/1995 | Corless et al. | |
| 5,562,642 A * | 10/1996 | Smith et al. .................. | 604/289 |
| 5,632,996 A | 5/1997 | Ramirez et al. | |
| 5,648,389 A | 7/1997 | Gans et al. | |
| 5,660,839 A | 8/1997 | Allec et al. | |
| 5,690,946 A | 11/1997 | Koulbanis et al. | |
| 5,756,107 A | 5/1998 | Hahn et al. | |
| 5,756,119 A | 5/1998 | Deckner et al. | |
| 5,767,098 A | 6/1998 | Klein et al. | |
| 5,821,209 A | 10/1998 | Distaso et al. | |
| 5,821,237 A * | 10/1998 | Bissett et al. .................. | 514/75 |
| 5,849,834 A | 12/1998 | Matsuzaki et al. | |
| 5,874,074 A | 2/1999 | Smith | |

(Continued)

FOREIGN PATENT DOCUMENTS

EP 0335115 A2 10/1989

(Continued)

*Primary Examiner*—Isis A Ghali
(74) *Attorney, Agent, or Firm*—William J. McNichol; Reed Smith LLP (57) ABSTRACT

The present invention is a delivery system comprising a pad and a liquid composition, comprising an insoluble dermatologically active ingredient with a viscosity that permits substantially uniform absorption of the composition onto the pad, and the pad is in then packaged in a sealed container.

24 Claims, 5 Drawing Sheets
(4 of 5 Drawing Sheet(s) Filed in Color)

| | (A) | - | (B) | = | (C) | (B) | - | (D) | = | (E) | (C) | - | (F) | = | (G) | RATIO |
|---|---|---|---|---|---|---|---|---|---|---|---|---|---|---|---|---|
| | Total Weight | | - Med Pad Weight | | = Wet Empty Pouch | Med Pad Weight | | -Dry Pad Weight | | = Med on Pad | Wet Empty Pouch Wt | | - Dry Empty Pouch | | = Med On Pouch Walls & Voids | E/G |
| IA | 2.40 | - | 1.25 | = | 1.15 | 1.25 | - | 0.32 | = | 0.93 | 1.15 | - | 1.11 | = | 0.04 | 37.2 |
| IB | 2.40 | - | 1.24 | = | 1.16 | 1.24 | - | 0.31 | = | 0.93 | 1.16 | - | 1.11 | = | 0.05 | 18.6 |
| IC | 2.52 | - | 1.38 | = | 1.14 | 138 | - | 0.33 | = | 1.05 | 1.14 | - | 1.11 | = | 0.03 | 35.0 |
| IIA | 2.36 | - | 1.41 | = | 0.95 | 1.41 | - | 0.33 | = | 1.08 | 0.95 | - | 0.92 | = | 0.03 | 36.0 |
| IIB | 2.45 | - | 1.48 | = | 0.87 | 1.48 | - | 0.33 | = | 1.15 | 0.97 | - | 0.90 | = | 0.07 | 16.4 |
| IIC | 2.35 | - | 1.40 | = | 0.95 | 1.40 | - | 0.34 | = | 1.06 | 0.95 | - | 0.91 | = | 0.04 | 26.5 |
| IIIA | 2.49 | - | 1.32 | = | 1.17 | 1.32 | - | 0.33 | = | 0.99 | 1.17 | - | 1.07 | = | 0.10 | 9.9 |
| IIIB | 2.82 | - | 1.62 | = | 1.20 | 1.20 | - | 0.33 | = | 0.87 | 1.20 | - | 1.06 | = | 0.14 | 6.2 |

U.S. PATENT DOCUMENTS

| | | | |
|---|---|---|---|
| 5,880,079 A | 3/1999 | Polotti et al. | |
| 5,951,991 A | 9/1999 | Wagner et al. | |
| 5,958,436 A | 9/1999 | Hahn et al. | |
| 5,997,885 A | 12/1999 | Koulbanis et al. | |
| 6,001,380 A | 12/1999 | Smith et al. | |
| 6,017,549 A | 1/2000 | Knight et al. | |
| 6,113,921 A | 9/2000 | Friedman et al. | |
| 6,149,926 A | 11/2000 | Venkitaraman et al. | |
| 6,153,208 A | 11/2000 | McAtee et al. | |
| 6,183,766 B1 * | 2/2001 | Sine et al. | 424/405 |
| 6,338,855 B1 * | 1/2002 | Albacarys et al. | 424/409 |
| 6,413,536 B1 | 7/2002 | Gibson et al. | |
| 6,429,231 B1 | 8/2002 | Bhagwat et al. | |
| 6,455,076 B1 | 9/2002 | Hahn et al. | |
| 6,462,025 B2 | 10/2002 | Vishnupad | |
| 6,469,227 B1 | 10/2002 | Cooke et al. | |
| 6,784,145 B2 * | 8/2004 | Delambre et al. | 510/130 |
| 6,861,397 B2 * | 3/2005 | Seitz et al. | 510/119 |

FOREIGN PATENT DOCUMENTS

| | | |
|---|---|---|
| EP | 0413528 A1 | 2/1991 |
| WO | WO 94/13354 A | 6/1994 |
| WO | WO 95/23587 A | 9/1995 |
| WO | WO 97/15282 A | 5/1997 |

* cited by examiner

| | (A) Total Weight | - | (B) Med Pad Weight | = | (C) Wet Empty Pouch | (B) Med Pad Weight | - | (D) Dry Pad Weight | = | (E) Med on Pad | (C) Wet Empty Pouch Wt | - | (F) Dry Empty Pouch | = | (G) Med On Pouch Walls & Voids | RATIO E/G |
|---|---|---|---|---|---|---|---|---|---|---|---|---|---|---|---|---|
| IA | 2.40 | - | 1.25 | = | 1.15 | 1.25 | - | 0.32 | = | 0.93 | 1.15 | - | 1.11 | = | 0.04 | 37.2 |
| IB | 2.40 | - | 1.24 | = | 1.16 | 1.24 | - | 0.31 | = | 0.93 | 1.16 | - | 1.11 | = | 0.05 | 18.6 |
| IC | 2.52 | - | 1.38 | = | 1.14 | 138 | - | 0.33 | = | 1.05 | 1.14 | - | 1.11 | = | 0.03 | 35.0 |
| IIA | 2.36 | - | 1.41 | = | 0.95 | 1.41 | - | 0.33 | = | 1.08 | 0.95 | - | 0.92 | = | 0.03 | 36.0 |
| IIB | 2.45 | - | 1.48 | = | 0.87 | 1.48 | - | 0.33 | = | 1.15 | 0.97 | - | 0.90 | = | 0.07 | 16.4 |
| IIC | 2.35 | - | 1.40 | = | 0.95 | 1.40 | - | 0.34 | = | 1.06 | 0.95 | - | 0.91 | = | 0.04 | 26.5 |
| IIIA | 2.49 | - | 1.32 | = | 1.17 | 1.32 | - | 0.33 | = | 0.99 | 1.17 | - | 1.07 | = | 0.10 | 9.9 |
| IIIB | 2.82 | - | 1.62 | = | 1.20 | 1.20 | - | 0.33 | = | 0.87 | 1.20 | - | 1.06 | = | 0.14 | 6.2 |

DELIVERY SYSTEM FOR TOPICAL MEDICATIONS

FIELD OF THE INVENTION

The present invention relates to drug delivery systems. In particular, it relates to such systems which comprise pads, sealed containers and liquid compositions.

BACKGROUND OF THE INVENTION

Dermatologically active ingredients for topical application to human skin are often insoluble solids (also called particulates) in media that are acceptable for skin application, e.g. without limitation, benzoyl peroxide ("BPO"), and insoluble antifungals. In order to prepare these topical products, dermatologically active ingredients are often suspended in the vehicle, which may be, for example without limitation, gels, creams, or lotions.

It is also desirable to have these types of dermatologically active ingredients placed on pads for delivery by wiping the pad on the skin. Pads may additionally be disposable for both convenience and sanitary reasons. However, several problems exist with this approach when it is applied to dermatologically active ingredients that are insoluble, minimally or weakly soluble.

First, the dermatologically active ingredient compositions, e.g. without limitation, BPO compositions, are not uniformly deposited on the pad. Second, the dermatologically active ingredient composition are not uniformly deposited on the skin during the wiping of the pad across the skin. Without uniformity, one cannot predict how much and whether any of the dermatologically active ingredient is delivered, and therefore, the delivery method is ineffective. Specified uniformity is preferred in most drug delivery systems.

Factors that are relevant to these problems include, that a portion of the liquid composition may preferentially squeeze through the fibers of the pad, leaving a high concentration of particulate dermatologically active ingredients on a surface of the pad. On the other hand, dermatologically active ingredient particles may preferentially squeeze through the fibers and leave particles on the walls of the container or in some parts of the pad or container, but not others.

Additionally, the container for a BPO pad, for example, may contribute to these problems. If the container is sealed with an alkaline based adhesive, BPO, a strong oxidizing agent, dissolves the adhesive after being in contact with BPO for as little as a month. The adhesive seal degrades and the two halves of the pouch come apart. Thus, there is also a need for a leak-proof container.

The use of pads stored in jars or large containers to apply single-phase solutions of dermatologically active ingredients has long been known as an effective technique. Because the dermatologically active ingredient is in solution, it remains acceptably distributed throughout the solvent vehicle, and is not susceptible to removal from the solution by filtration or adsorption by the pad.

The use of pads to apply single-phase suspensions of dermatologically active ingredients has been unsuccessful. The suspended dermatologically active ingredient tends to settle to the bottom of the container, resulting in unacceptable variations in dermatologically active ingredient concentration. This problem is aggravated by the tendency of pads to filter out or adsorb the suspended dermatologically active ingredient. Thus, even if the dermatologically active ingredient does not settle out of suspension, it can be collected on the pads unevenly. To make matters worse, having filtered or adsorbed the dermatologically active ingredient out of suspension, such pads have a tendency to retain the dermatologically active ingredient and not release it to the skin.

Oil-in-water and water-in-oil emulsions (e.g. without limitation creams and lotions) have been used as delivery vehicles for suspensions of dermatologically active ingredients (e.g. TRIAZ® of Medicis Pharmaceutical Corp. of Arizona) and work well when used alone as delivery vehicles. These creams and lotions hold the dermatologically active ingredients in suspension fairly well, resulting in even distribution of the dermatologically active ingredient throughout the vehicle, and thus on the skin.

However, when pads or pledgets are used to topically apply creams or lotions, several problems have been encountered. Creams have been found to adhere poorly to pads, and adhere all too well to the pad's container. Attempts to use pads as a delivery vehicle have resulted in the pads being used to wipe or scrape the cream or lotion off the container's walls so that it can be applied to the skin, and often the cream is incompletely released from the pad resulting in under-application of the dermatologically active ingredients. This has been a source of great frustration in the drug delivery art, as pads are a highly desirably method of topical application. For example, in the field of acne treatments, pads have been used for decades to apply solutions of salicylic acid (e.g. Stri-Dex® of Blistex Inc. of Illinois). On the other hand, benzoyl peroxide, which has been known for decades as a superior treatment for acne, has never been successfully marketed with a pad delivery system because it is not soluble and is delivered as a suspension in a cream or lotion. Thus, there is a great and long-standing demand for a way to topically deliver particle suspension of dermatologically active ingredients by way of a pad.

SUMMARY OF THE INVENTION

The present invention overcomes many of the problems experienced in the art. In this invention, the dermatologically active ingredients are insoluble drugs suitable for human or animal use, and the composition is a liquid comprising one or more dermatologically active ingredients. The composition is retained by the pad preferentially over the container. Dermatologically active ingredients, e.g. without limitation, BPO, and insoluble antifungals, do not preferentially migrate or adsorb from the composition (e.g. without limitation, emulsion) onto or into the pad, and therefore does not result in an uneven concentration of the dermatologically active ingredient in the composition versus the pad. Further, the pad is packaged in a container and one or more pads may be packaged in each container.

In this invention, pads include but are not limited to pads, pledgets, towels, towelettes, cloths, and sponges; the pads may be woven or nonwoven material. The dermatologically active ingredients in the invention can be any particulate or insoluble drugs including but not limited to drugs, prodrugs, cosmeceuticals, herbal medicines, traditional medicines, and active cosmetic ingredients, that are suitable for topical human use and are suspended and/or dispersed in a vehicle. Insoluble in this specification means insoluble or weakly or minimally soluble. Insoluble dermatologically active ingredients are often particulates.

In accordance with the present invention, insoluble dermatologically active ingredients are mixed in an emulsion composition, e.g. without limitation, an oil-in-water emulsion or a water-in-oil emulsion, preferably an oil-in-water emulsion. This composition is suited to causing the dermatologically active ingredient to be substantially uniformly distributed throughout the composition upon routine mixing during formulation, and remain so during the product's shelf life. The particle size may preferably be up to about 300 microns, more preferably about 10 to about 150 microns. For BPO, the most preferable particle size is less than about 50 microns. Further, the viscosity of the composition is carefully adjusted to be low enough that the composition will permeate the matrix of the pad's fibers and be held on the pad by capillary action. However, the viscosity must not be so low that the composition is so thin that it drains off the pad prematurely. On the other hand, if the viscosity is too high, not only will the composition fail to be taken into the pad's fibers' matrix, it will tend to be released from the surface of the pad to the walls of the container, and remain there, unavailable for application to the patient's skin.

Use of the present invention by wiping the pad across skin results in a transfer to the skin of the dermatologically active ingredient, meaning that the skin is substantially uniformly medicated. During this wiping, an adequate therapeutic dose of the dermatologically active ingredient is delivered to the skin. One advantage of this invention may be a reduced irritation to the skin as compared to similar compositions applied without the pad.

The composition may comprise one or more dermatologically active ingredients. The dermatologically active ingredient may be any drug effective in dermatological prevention or treatment, which is insoluble in the composition and is a particulate. An effective amount of the dermatologically active ingredient means an adequate therapeutic dose will be delivered to the skin by wiping the pad onto the skin.

The dermatologically active ingredient may be one or more dermatological drug which is insoluble in the composition, such as without limitation, drugs to treat or prevent acne, fungal infections, yeast infections, rosacea, photodamaged skin, hyperpigmented skin, eczema, allergic or contact dermatitis, seborrheic dermatitis, erythema, or psoriasis; salts or chelates, such as without limitation zinc oxide, iron EDTA, magnesium peroxide, ascorbyl linoleate; abrasives; active acids; active bases, such as without limitation minocycline; neutral actives, such as without limitation hydrocortisone; BPO; antifungals; antibacterials; corticosteroids; keratolytic agents; sulfur; sulfur-containing ingredients; or combinations thereof.

In one embodiment, soluble dermatologically active ingredients may additionally be present in the composition.

BRIEF DESCRIPTION OF THE DRAWINGS

The patent or application file contains at least one drawing executed in color. Copies of this patent or application publication with color drawing(s) will be provided by the Office upon request and payment of the necessary fee.

DETAILED DESCRIPTION OF THE SPECIFIC EMBODIMENTS

Pharmaceutical Compositions

One embodiment may comprise the composition with BPO as an dermatologically active ingredient, alone or in combination with other dermatologically active ingredients, in an oil-in-water emulsion. In one embodiment, the BPO particle size is less than about 50 microns, which provides substantially even coverage on the face and reduces the entrapment in the pad, e.g. without limitation, a non-woven pad. BPO in the composition may irritate sensitive skin and therefore, the composition may optionally comprise dimethicone, which may make the composition more acceptable for sensitive skin.

The composition may comprise one or more sulfur-containing ingredient as an dermatologically active ingredient, alone or in combination with other dermatologically active ingredients, in an oil-in-water emulsion in another embodiment. Sulfur-containing ingredients include without limitation sulfur and sulfacetamide.

An embodiment may comprise a composition with an insoluble antifungal as an dermatologically active ingredient alone or in combination with other dermatologically active ingredients, in an oil-in-water emulsion.

In one embodiment, the particle size of the dermatologically active ingredient may be reduced by milling the dermatologically active ingredient or end product, and/or the composition may have additional agents that substantially smooth the particle surface through a physical and/or chemical reaction. This may aid in substantially smooth application to the skin.

The composition of the present invention may be an oil-in-water emulsion with a viscosity of about 500 cps to about 7000 cps, more preferably about 2000 cps to about 3000 cps, and most preferably about 2200 cps. This viscosity is measured by a Brookfield viscometer LVT model at about 27° C. for sixty seconds. Most of the measurements were taken with a spindle set for 30 rpm, and some set for 12 rpm (if the composition was too thick for the 30 rpm), and then each was converted into cps. All of the viscosity measurements and limitations in this application are calculated in this same manner, unless otherwise specified.

Pads

Pads of this invention may be made of synthetic or natural material and woven or non-woven material, for example without limitation, BBA Nonwovens Product No. 149-273, which is 76 gsy (gsy means grams per square yard) of 46% rayon/54% polypropylene composite, 7 dot pattern, thermal bonded fabric made by BBA Nonwoven Division Bethune, S.C. Materials for the pad may comprise more than one layer.

In one embodiment, the pad is a non-woven material in a circular shape of 2.5 inches in diameter. The composition in this embodiment may be BPO in a oil-in-water emulsion.

In a preferred embodiment, the composition is an emulsion which is optimized to avoid demulsification when the composition is applied to the pad.

Containers

Packaging for the pad has an additional set of considerations. A container may contain one or more pads, does not leak the composition nor does it degrade excessively over time once it is sealed. The present invention may, for example without limitation, have a container comprised of a foil material with an inner plastic layer, such as Pechiney Corporation's of France packaging material composed of Varnish/ink/ paper/LDPE/aluminum foil/Surlyn® (E.I. DuPont DeNemours & Co.); or Bomarko, Inc. of Indiana's packaging material composed of BLMG/LD/285F/MCMT. LDPE means low density polyethylene. In one embodiment of the invention, a container of foil material lined with a plastic was heat-sealed on four sides of a rectangle at 250° F. to 350° F. for a few seconds melting the plastic and forming a strong bond that remained intact for at least three (3) months under accelerated conditions (about 40° C. and 75% relative humidity), which typically corresponds to about 18 to about 24 months at room temperature (about 25° C.).

In an embodiment of the invention, the container may be any material that packages the pad with the composition and does not degrade or leak the composition for a sufficient period of time, such as shelf life of the invention. Preferably, the container comprises one or more sheets of plastic-lined foil material. The container is fashioned from the sheets to hold one or more pads. In one embodiment, two sheets, which are larger than the pad or the dimensions of the pad when folded, are placed in the following layers: a bottom sheet, the pad, and the top sheet over the pad. The sides of the sheets meet because the pad is smaller than the sheets and is placed in the center of the sheets. At the sides of the sheets, heat and pressure (preferably about 15 psi to about 40 psi) is applied which causes the plastic lining of both sheets to melt and seal together, enclosing the pad. One of ordinary skill in the art will understand that time, heat and pressure will vary according to the type of material and/or process used.

Further Embodiments and Parts Thereof

In one embodiment of the invention, the delivery system comprises a pad, a sealed container, and a composition, wherein the composition may be an emulsion which is substantially absorbed via capillary action to the pad, and the composition substantially remains on the pad in the container and a therapeutic amount of medication in the composition is discharged to the skin upon wiping the pad across the skin.

BPO is preferably 75% and sold under the trademarks LUPEROX® A75FP/LUPERSOL® 75FP by ATOFINA® or LUCIDOL® 75.

Table I depicts three embodiments (I, II, III) of the composition used in the present invention.

TABLE 1

|  |  | I | II | III |
|---|---|---|---|---|
| Dry flo starch |  | 1 | 1 | 1 |
| LUCIDOL ® 75 | Benzoyl peroxide 75% | 4.72 | 9.2 | 13.8 |
| CARBOPOL ® ultrez 10 | Carbomer | 0.3 | 0.3 | 0.3 |
| VERSENE ® NA | Disodium EDTA | 0.5 | 0.5 | 0.5 |
| Deionized water |  | 71.78 | 67.3 | 62.6 |
| Glycerin 99% |  | 6 | 6 | 6 |
| Sodium hydroxide pellets |  | 0.3 | 0.3 | 0.3 |
| PURAMEX ® ZN | Zinc lactate | 0.2 | 0.2 | 0.2 |
| Glycopure 70% | Glycolic acid | 0.5 | 0.5 | 0.5 |
| Finsolve TN | $C_{12}$-$C_{15}$ alkyl benzoate | 7.1 | 7.1 | 7.1 |
| Cetearyl alcohol |  | 2 | 2 | 2 |
| Dimethicone |  | 1 | 1 | 1 |
| ARLACEL ® 165 | Glyceryl stearate & PEG 100 stearate | 1 | 1 | 1 |
| BRIJ ® 72 | Stearth 2 | 1.5 | 1.5 | 1.5 |
| BRIJ ® 78 | Stearth 20 | 1 | 1 | 1 |
| TWEEN ® 20 | Polysorbate 20 | 1.1 | 1.1 | 1.2 |

As is known in the art, the following definitions apply to this specification. EDTA means ethylenediamine tetraacetic acid. PEG means polyethylene glycol. BHT means butylated hydroxytoluene.

Test 1

Figure 1:
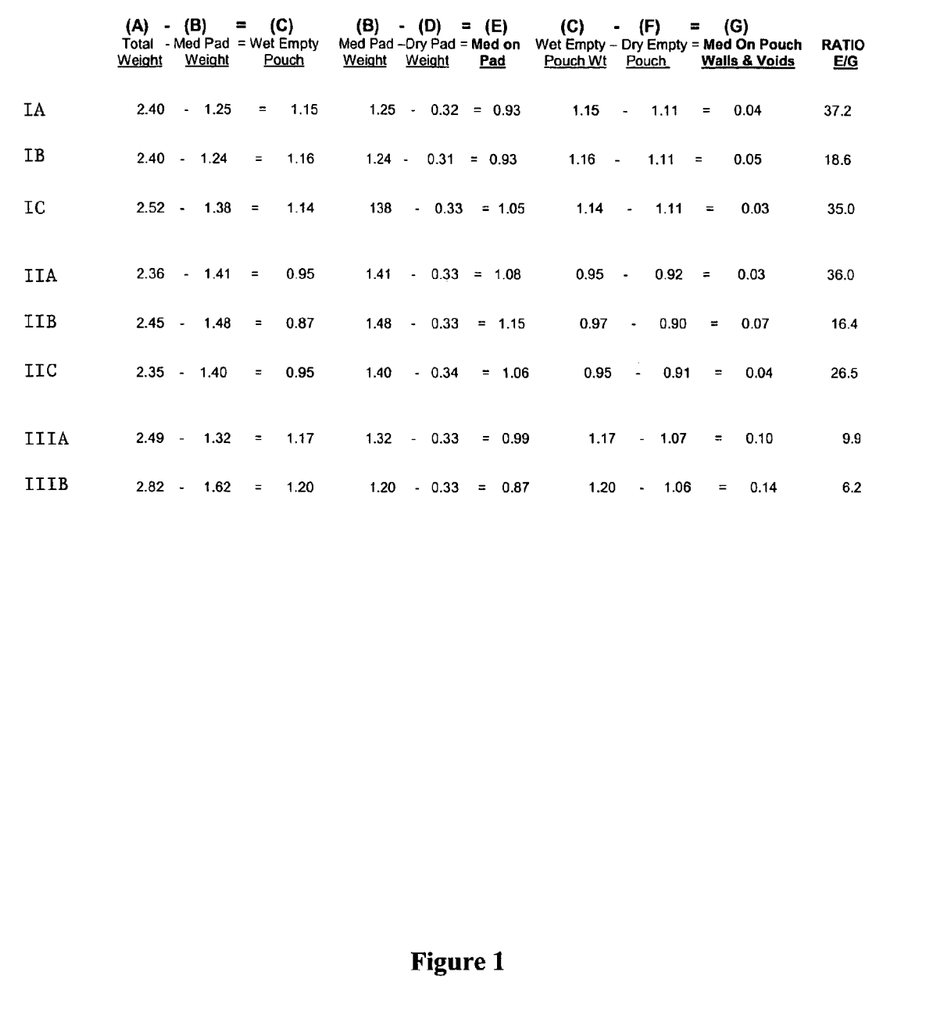
FIG. 1 depicts the amount of composition associated with the pad and with the wall and void spaces of the container.

FIG. 1 depicts the results of a test performed to see whether the BPO was excessively transferred from the pad to the inside of the container. Pads with compositions in Examples I (three times IA, IB, and IC), II (three times IIA, IIB, and IIC) and III (two times IIIA and IIIB) were sealed in containers. The sealed containers were weighed ("Total Weight"), then after opening, the pad was weighed ("Med Pad Wt"). "C" or "Wet Empty Pouch" was then calculated.

Then, the pads were soaked with acetonitrile to remove the emulsion and BPO. This was repeated twice, and then the pads were dried to a constant weight ("Dry Pad Wt"). The "Med on Pad" or the composition available for transfer from the pad to the skin was calculated. Then, the containers were rinsed and dried to constant weight ("Dry, Empty Pouch"). The weight of the composition left on the container and therefore unavailable to transfer to the skin was then calculated ("Med on Pouch Walls & Voids"). It is preferred that the ratio of (Med on Pad) to (Med on Pouch Walls & Voids) is 5 or greater.

Test 2

In a separate test, 0.15% (all percentages given in this specification are weight percentages unless otherwise specified) fluorescein sodium was added as a marker to compositions of Example I, to test whether the composition applies uniformly to the skin via the pad. Subjects were given the composition alone and asked to apply it to their faces and foreheads for comparison purposes.

In a separate procedure, subjects wiped the pads on their faces and foreheads. They were asked to use such pads in the same manner that they used other facial cleansing or medicated products. No other attempt was made to influence how the subjects were to wipe the skin.

Figure 2:
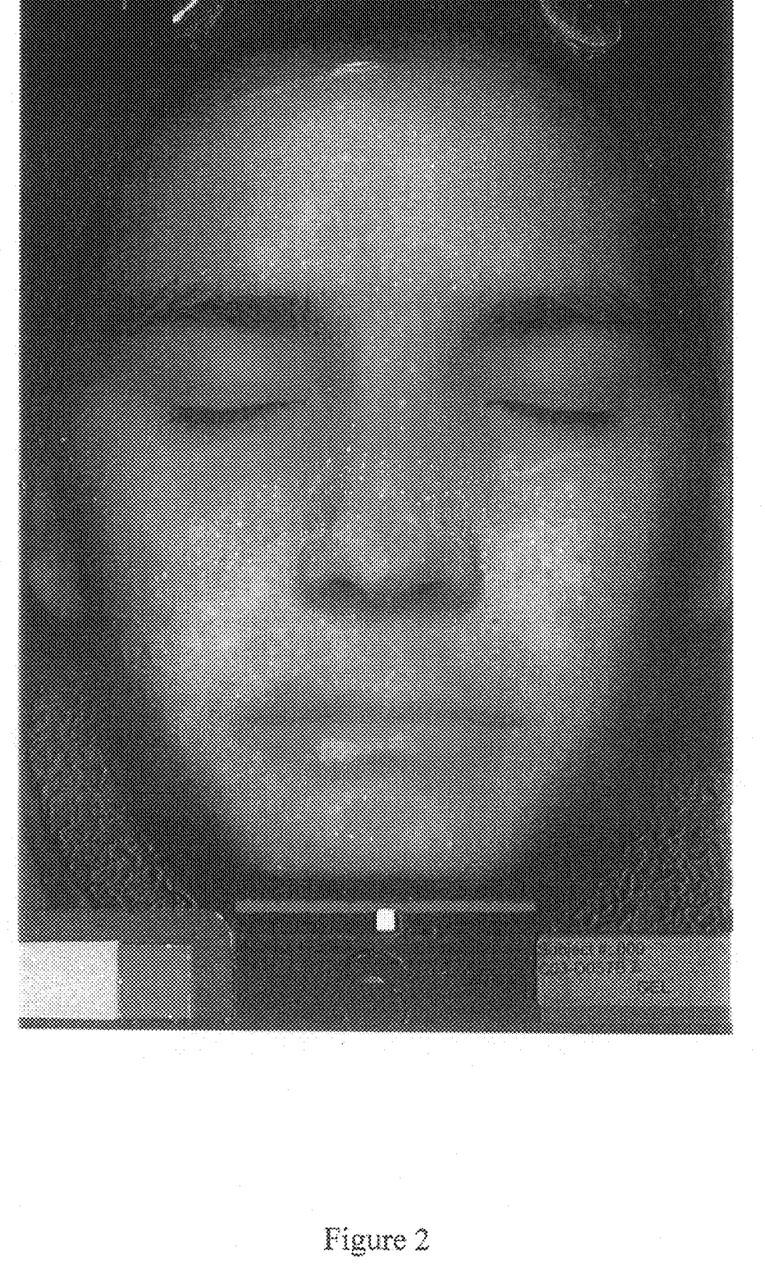
FIG. 2 is a ultra-violet photograph of Subject A in Test 2 after the composition was applied directly, not via a pad.
Figure 3:
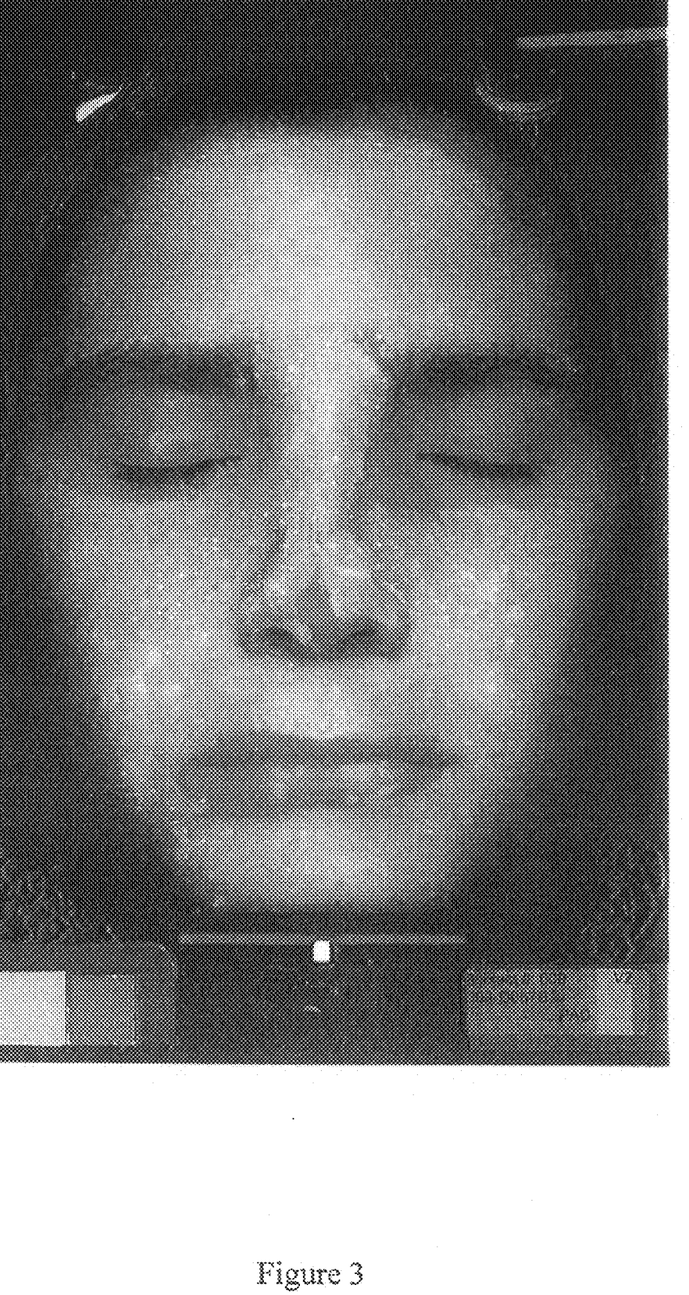
FIG. 3 is a ultra-violet photograph of Subject A in Test 2 after the composition was applied via the pad.

Thirty minutes after each application (the composition alone and the composition via the pad), ultra-violet photographs were taken of the subject's face and foreheads. They showed substantially smooth and uniform deposition of the medication via the pad. FIG. 2 depicts Subject A after the composition was applied directly, and FIG. 3 depicts Subject A after the composition was applied via the pad. FIG. 2 shows that little or none of the composition was delivered to significant areas of the skin, and that there were isolated areas of excessive application. FIG. 3 shows that all areas where the subject applied the pad received sufficient composition.

Figure 4:
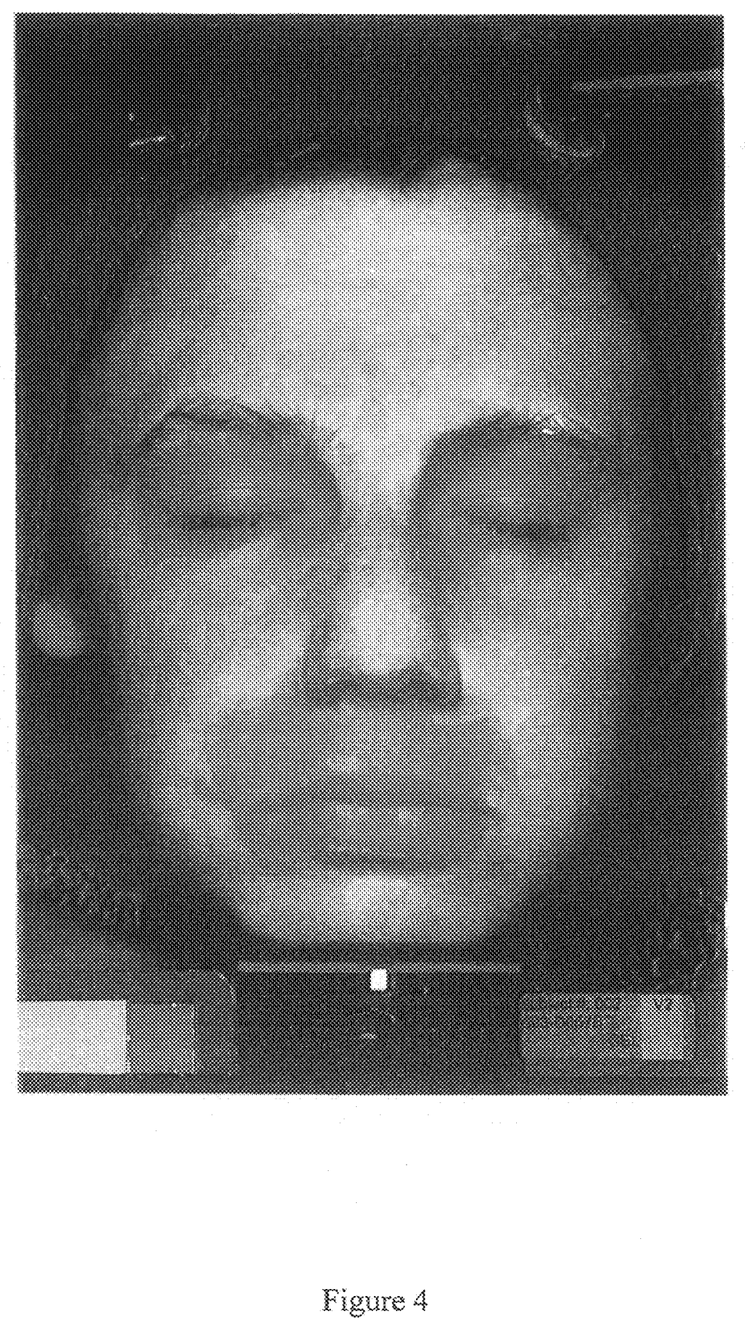
FIG. 4 is a ultra-violet photograph of Subject B in Test 2 after the composition was applied directly, not via a pad.
Figure 5:
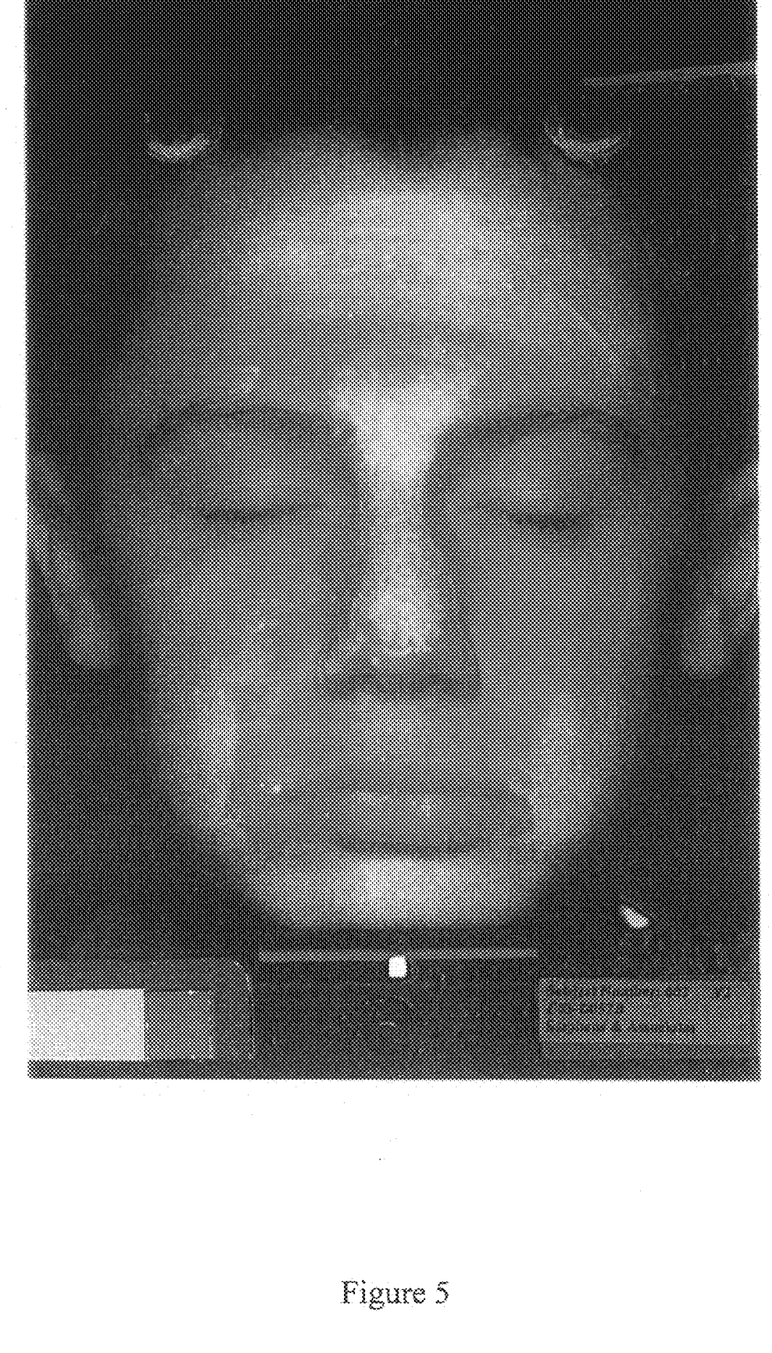
FIG. 5 is a ultra-violet photograph of a Subject B in Test 2 after the composition was applied via the pad.

FIG. 4 depicts Subject B after the composition was applied directly, and FIG. 5 depicts Subject B after the composition was applied via the pad. FIG. 4 shows that there were significant areas where little or no composition was delivered and several locations of clumps or excessive application. FIG. 5 shows that all areas where the subject applied the pad received sufficient composition.

Test 3

Separately, the pads were used to test whether acceptable levels of medication are applied to the skin from the pads. Regulatory boards and workers in the art have described an acceptable level of topical medication applied to the skin as being in the range of at least 2 mg of total medication, including the vehicle, covering each square centimeter of skin. In this test, subjects applied pads with Examples I and III to a prescribed area of the face in the same manner as they would normally use such medicated pads. To determine the amount of composition applied to this area of skin (which was 80 to 100 square centimeters), the pad was weighed before and after it was used. The weight of medication used was calculated and then divided by the area of skin.

For Example I pads, the mean dose of total composition delivered was 2.9 to 3.875 mg/cm². For Example III, the mean dose of total composition delivered was 2.10 to 2.625 mg/cm².

Test 4

Several sample embodiments of the present invention were also tested to obtain the viscosity. Each example was tested as described in paragraph 21. The results of these tests are as follows. Example I had a viscosity of 2000-2800 cps, Example II had a viscosity of 2000-2400 cps, Example III had a viscosity of 2000-2500 cps, and other compositions had the following viscosity.

TABLE 2

| | | IV | V | VI | VII |
|---|---|---|---|---|---|
| Dry flo starch | | 1 | 1 | 1 | 1 |
| Lucidol 75 | Benzoyl peroxide | 4.72 | 4.72 | 9.2 | 13.8 |
| Carbopol ultrez 10 | Carbomer | 0.3 | 0.3 | 0.3 | 0.3 |
| Versene NA | Disodium EDTA | 0.5 | 0.5 | 0.5 | 0.5 |
| Deionized water | | 71.58 | 71.48 | 66.7 | 62.6 |
| Glycerin 96% | | 6 | 6 | 6 | 6 |
| Sodium hydroxide pellets | | 0.3 | 0.3 | 0.3 | 0.3 |
| Puramex ZN | Zinc lactate | 0.2 | 0.2 | 0.2 | 0.2 |
| Glycopure 70% | Glycolic acid | 0.5 | 0.5 | 0.5 | 0.5 |
| Finsolve TN | C$_{12}$-C$_{15}$ alkyl benzoate | 7.1 | 7.1 | 7.1 | 7.1 |
| Dimethicone | | 1 | 1 | 1 | 1 |
| Crodacol CS-50 | Cetyl stearyl alcohol | 2.3 | 2.4 | 2.2 | 2 |
| Arlacel 165 | Glyceryl stearate & PEG 100 stearate | 1 | 1 | 1.5 | 1 |
| Brij 72 | Steareth 2 | 1.5 | 1.5 | 1.5 | 1.5 |
| Brij 78 | Steareth 20 | 1 | 1 | 1 | 1 |
| Tween 20 | Polysorbate 20 | 1 | 1 | 1 | 1.2 |
| Viscosity (cps) | | 2200 | 6600 | 3400 | 2600 |

Additionally, the compositions of the present invention may be tested for viscosity in the following manner. A Brookfield viscometer model No. RVT with spindle #4 at 20 rpm for 60 seconds will be used at 25° C.+/−1° C. In this test, the compositions are preferably about 500 cps to about 10,000 cps, more preferably about 1900 cps to about 7000 cps, most preferably 4500 to about 6500 cps.

It is to be understood that while the invention has been described in conjunction with the detailed description thereof, that the foregoing description is intended to illustrate and not limit the scope of the invention, which is defined by the scope of the appended claims. Other aspects, advantages, and modifications are evident from a review of the following claims.

What is claimed is:

1. A drug delivery system comprising
   a pad;
   a container; and
   a liquid composition, wherein the composition comprises:
   (1) an effective amount of one or more insoluble dermatologically active ingredients, and (2) an emulsion vehicle for the dermatologically active ingredients,
   wherein the composition has a viscosity which is low enough for the composition to substantially uniformly absorb onto the pad via capillary action, and high enough to be substantially retained on the pad, not the container, and
   wherein the active ingredient comprises benzoyl peroxide particles of less than 50 microns.

2. A drug delivery system comprising
   a pad;
   a container; and
   a liquid composition, wherein the composition comprises:
   (1) an effective amount of one or more insoluble dermatologically active ingredients, and (2) an emulsion vehicle for the dermatologically active ingredients,
   wherein the composition has a viscosity which is low enough for the composition to substantially uniformly absorb onto the pad via capillary action, and high enough to be substantially retained on the pad, not the container, and wherein the active ingredient comprises particles of about 10 to about 150 microns.

3. The system of claim 1 wherein the composition has a viscosity of about 500 to about 9000 cps measured on a Brookfield viscometer LVT model at about 27° C. for 60 seconds and a spindle set for 30 rpm.

4. The system of claim 1 wherein the composition has a viscosity of about 2000 cps to about 3000 cps measured on a Brookfield viscometer LVT model at about 27° C. for 60 seconds and a spindle set for 30 rpm.

5. The system of claim 1 wherein the composition has a viscosity of about 500 to about 10,000 cps measured on a Brookfield viscometer RVT model with spindle #4 at 20 rpm for 60 seconds at 25° C.+−1° C.

6. The system of claim 1 wherein the composition has a viscosity of about 1900 to about 7,000 cps measured on a Brookfield viscometer RVT model with spindle #4 at 20 rpm for 60 seconds at 25° C.+−1° C.

7. The system of claim 1 wherein the composition has a viscosity of about 4500 to about 6,500 cps measured on a Brookfield viscometer RVT model with spindle #4 at 20 rpm for 60 seconds at 25° C.+−1° C.

8. A drug delivery system comprising
   a pad;
   a container; and
   a liquid composition, wherein the composition comprises:
   (1) an effective amount of one or more insoluble dermatologically active ingredients, and (2) an emulsion vehicle for the dermatologically active ingredients,
   wherein the composition has a viscosity which is low enough for the composition to substantially uniformly absorb onto the pad via capillary action, and high enough to be substantially retained on the pad, not the container, and wherein the active ingredient comprises particles of up to about 300 microns.

9. A drug delivery system comprising
   a pad;
   a container; and
   a liquid composition, wherein the composition comprises:
   (1) an effective amount of one or more insoluble dermatologically active ingredients, and (2) an emulsion vehicle for the dermatologically active ingredients,
   wherein the composition has a viscosity which is low enough for the composition to substantially uniformly absorb onto the pad via capillary action, and high enough to be substantially retained on the pad, not the container, and wherein the active ingredient comprises particles of less than 50 microns.

10. The system of claim 2 wherein the composition has a viscosity of about 500 to about 9000 cps measured on a Brookfield viscometer LVT model at about 27° C. for 60 seconds and a spindle set for 30 rpm.

11. The system of claim 2 wherein the composition has a viscosity of about 2000 cps to about 3000 cps measured on a Brookfield viscometer LVT model at about 27° C. for 60 seconds and a spindle set for 30 rpm.

12. The system of claim 2 wherein the composition has a viscosity of about 500 to about 10,000 cps measured on a Brookfield viscometer RVT model with spindle #4 at 20 rpm for 60 seconds at 25° C.+−1° C.

13. The system of claim 2 wherein the composition has a viscosity of about 1900 to about 7,000 cps measured on a Brookfield viscometer RVT model with spindle #4 at 20 rpm for 60 seconds at 25° C.+−1° C.

14. The system of claim 2 wherein the composition has a viscosity of about 4500 to about 6,500 cps measured on a Brookfield viscometer RVT model with spindle #4 at 20 rpm for 60 seconds at 25° C.+−1° C.

15. The system of claim 8 wherein the composition has a viscosity of about 500 to about 9000 cps measured on a Brookfield viscometer LVT model at about 27° C. for 60 seconds and a spindle set for 30 rpm.

16. The system of claim 8 wherein the composition has a viscosity of about 2000 cps to about 3000 cps measured on a Brookfield viscometer LVT model at about 27° C. for 60 seconds and a spindle set for 30 rpm.

17. The system of claim 8 wherein the composition has a viscosity of about 500 to about 10,000 cps measured on a Brookfield viscometer RVT model with spindle #4 at 20 rpm for 60 seconds at 25° C.+−1° C.

18. The system of claim 8 wherein the composition has a viscosity of about 1900 to about 7,000 cps measured on a Brookfield viscometer RVT model with spindle #4 at 20 rpm for 60 seconds at 25° C.+−1° C.

19. The system of claim 8 wherein the composition has a viscosity of about 4500 to about 6,500 cps measured on a Brookfield viscometer RVT model with spindle #4 at 20 rpm for 60 seconds at 25° C.+−1° C.

20. The system of claim 9 wherein the composition has a viscosity of about 500 to about 9000 cps measured on a Brookfield viscometer LVT model at about 27° C. for 60 seconds and a spindle set for 30 rpm.

21. The system of claim 9 wherein the composition has a viscosity of about 2000 cps to about 3000 cps measured on a Brookfield viscometer LVT model at about 27° C. for 60 seconds and a spindle set for 30 rpm.

22. The system of claim 9 wherein the composition has a viscosity of about 500 to about 10,000 cps measured on a Brookfield viscometer RVT model with spindle #4 at 20 rpm for 60 seconds at 25° C.+−1° C.

23. The system of claim 9 wherein the composition has a viscosity of about 1900 to about 7,000 cps measured on a Brookfield viscometer RVT model with spindle #4 at 20 rpm for 60 seconds at 25° C.+−1° C.

24. The system of claim 9 wherein the composition has a viscosity of about 4500 to about 6,500 cps measured on a Brookfield viscometer RVT model with spindle #4 at 20 rpm for 60 seconds at 25° C.+−1° C.

* * * * *

(12) EX PARTE REEXAMINATION CERTIFICATE (9224th)
United States Patent
Patel et al.

(10) Number: US 7,776,355 C1
(45) Certificate Issued: Aug. 21, 2012

(54) DELIVERY SYSTEMS FOR TOPICAL MEDICATIONS

(75) Inventors: Bhiku G. Patel, Chandler, AZ (US);
Mohan Vishnupad, Easton, CT (US);
Eugene H. Gans, Westport, CT (US);
Kuljit S. Bhatia, Chandler, AZ (US)

(73) Assignee: Medics Pharmaceutical Corporation, Scottsdale, AZ (US)

Reexamination Request:
No. 90/011,226, Oct. 7, 2010

Reexamination Certificate for:
Patent No.: 7,776,355
Issued: Aug. 17, 2010
Appl. No.: 10/613,698
Filed: Jul. 3, 2003

(51) Int. Cl.
*A61F 13/00* (2006.01)
*A61K 8/00* (2006.01)

(52) U.S. Cl. .................. 424/443; 424/401; 424/449
(58) Field of Classification Search ................ None
See application file for complete search history.

(56) References Cited

To view the complete listing of prior art documents cited during the proceeding for Reexamination Control Number 90/011,226, please refer to the USPTO's public Patent Application Information Retrieval (PAIR) system under the Display References tab.

*Primary Examiner* — Johnny F Railey (57) ABSTRACT

The present invention is a delivery system comprising a pad and a liquid composition, comprising an insoluble dermatologically active ingredient with a viscosity that permits substantially uniform absorption of the composition onto the pad, and the pad is in then packaged in a sealed container.

EX PARTE REEXAMINATION CERTIFICATE ISSUED UNDER 35 U.S.C. 307

NO AMENDMENTS HAVE BEEN MADE TO THE PATENT

AS A RESULT OF REEXAMINATION, IT HAS BEEN DETERMINED THAT:

The patentability of claims 1-24 is confirmed.

* * * * *